(12) United States Patent
Lubock et al.

(10) Patent No.: US 8,177,792 B2
(45) Date of Patent: *May 15, 2012

(54) PLUGGED TIP DELIVERY TUBE FOR MARKER PLACEMENT

(75) Inventors: Paul Lubock, Laguna Niguel, CA (US); Jason H. Safabash, Aliso Viejo, CA (US); Martin Shabaz, Lake Forest, CA (US); John Merritt, San Clemente, CA (US)

(73) Assignee: Senorx, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/592,020

(22) Filed: Nov. 18, 2009

(65) Prior Publication Data

US 2010/0094169 A1    Apr. 15, 2010

Related U.S. Application Data

(63) Continuation of application No. 10/174,401, filed on Jun. 17, 2002, now Pat. No. 7,651,505.

(51) Int. Cl.
*A61B 17/00* (2006.01)

(52) U.S. Cl. ............ 606/116; 600/431; 600/432

(58) Field of Classification Search ........... 606/116, 606/117, 142; 600/3, 7, 407, 410, 420, 431, 600/433, 434, 562, 564, 567, 432, 426, 565; 604/59, 60, 93.01, 116, 164.01, 81.1, 61, 604/63, 199, 272, 274

See application file for complete search history.

(56) References Cited

U.S. PATENT DOCUMENTS

| | | | |
|---|---|---|---|
| 2,192,270 A | 3/1940 | McGowan | |
| 2,481,408 A | 9/1949 | Fuller et al. | |
| 2,832,888 A | 4/1958 | Houston | |
| 2,899,362 A | 8/1959 | Sieger, Jr. et al. | |
| 2,907,327 A | 10/1959 | White | |
| 3,341,417 A | 9/1967 | Sinaiko | |
| 3,402,712 A | 9/1968 | Eisenhand | |
| 3,516,412 A | 6/1970 | Ackerman | |

(Continued)

FOREIGN PATENT DOCUMENTS

DE    1029528 B    5/1958

(Continued)

OTHER PUBLICATIONS

Armstrong, J. S., et al., "Differential marking of Excision Planes in Screened Breast lesions By Organically Coloured Gelatins", *Journal of Clinical Pathology*, Jul. 1990, No. 43 (7) pp. 604-607, XP000971447 abstract; tables 1,2.

(Continued)

*Primary Examiner* — Tuan Nguyen

(57) ABSTRACT

An intracorporeal marker delivery device includes a delivery tube which has a tapered, tissue penetrating distal tip, an inclined discharge orifice in the tapered distal tip and an inner bore extending to the orifice. A plurality of remotely detectable markers, which are formed at least in part of bioresorbable material, are slidably disposed within the inner bore. A plug having an inclined exposed surface, which is formed at least in part of bioresorbable material, is releasably secured within the inner bore of the delivery tube distal to the plurality of remotely detectable markers disposed therein to retain the plurality of remotely detectable markers within the inner bore. The plug is disposed at least in part within the inclined discharge orifice. A plunger is slidably disposed within the inner bore proximal to the plurality of remotely detectable markers.

16 Claims, 8 Drawing Sheets

U.S. PATENT DOCUMENTS

| | | | |
|---|---|---|---|
| 3,593,343 A | 7/1971 | Viggers | |
| 3,757,781 A | 9/1973 | Smart | |
| 3,818,894 A | 6/1974 | Wichterle et al. | |
| 3,823,212 A | 7/1974 | Chvapil | |
| 3,921,632 A | 11/1975 | Bardani | |
| 4,005,699 A | 2/1977 | Bucalo | |
| 4,007,732 A | 2/1977 | Kvavle et al. | |
| 4,041,931 A | 8/1977 | Elliott et al. | |
| 4,103,690 A | 8/1978 | Harris | |
| 4,105,030 A | 8/1978 | Kercso | |
| 4,172,449 A | 10/1979 | LeRoy et al. | |
| 4,197,846 A | 4/1980 | Bucalo | |
| 4,217,889 A | 8/1980 | Radovan et al. | |
| 4,276,885 A | 7/1981 | Tickner et al. | |
| 4,294,241 A | 10/1981 | Miyata | |
| 4,298,998 A | 11/1981 | Naficy | |
| 4,331,654 A | 5/1982 | Morris | |
| 4,390,018 A | 6/1983 | Zukowski | |
| 4,400,170 A | 8/1983 | McNaughton et al. | |
| 4,401,124 A | 8/1983 | Guess et al. | |
| 4,405,314 A | 9/1983 | Cope | |
| 4,428,082 A | 1/1984 | Naficy | |
| 4,438,253 A | 3/1984 | Casey et al. | |
| 4,442,843 A | 4/1984 | Rasor et al. | |
| 4,470,160 A | 9/1984 | Cavon | |
| 4,487,209 A | 12/1984 | Mehl | |
| 4,545,367 A | 10/1985 | Tucci | |
| 4,582,061 A | 4/1986 | Fry | |
| 4,582,640 A | 4/1986 | Smestad et al. | |
| 4,588,395 A | 5/1986 | Lemelson | |
| 4,597,753 A | 7/1986 | Turley | |
| 4,647,480 A | 3/1987 | Ahmed | |
| 4,655,226 A | 4/1987 | Lee | |
| 4,661,103 A | 4/1987 | Harman | |
| 4,682,606 A | 7/1987 | DeCaprio | |
| 4,693,237 A | 9/1987 | Hoffman et al. | |
| 4,740,208 A | 4/1988 | Cavon | |
| 4,813,062 A | 3/1989 | Gilpatrick | |
| 4,820,267 A | 4/1989 | Harman | |
| 4,832,680 A * | 5/1989 | Haber et al. | 600/31 |
| 4,832,686 A | 5/1989 | Anderson | |
| 4,847,049 A | 7/1989 | Yamamoto | |
| 4,863,470 A | 9/1989 | Carter | |
| 4,870,966 A | 10/1989 | Dellon et al. | |
| 4,874,376 A | 10/1989 | Hawkins, Jr. | |
| 4,889,707 A | 12/1989 | Day et al. | |
| 4,909,250 A | 3/1990 | Smith | |
| 4,938,763 A | 7/1990 | Dunn et al. | |
| 4,950,665 A | 8/1990 | Floyd | |
| 4,963,150 A | 10/1990 | Brauman | |
| 4,970,298 A | 11/1990 | Silver et al. | |
| 4,989,608 A | 2/1991 | Ratner | |
| 4,994,028 A | 2/1991 | Leonard et al. | |
| 5,012,818 A | 5/1991 | Joishy | |
| 5,059,197 A | 10/1991 | Urie et al. | |
| 5,081,997 A | 1/1992 | Bosley, Jr. et al. | |
| 5,120,802 A | 6/1992 | Mares et al. | |
| 5,125,413 A | 6/1992 | Baran | |
| 5,137,928 A | 8/1992 | Erbel et al. | |
| 5,141,748 A | 8/1992 | Rizzo | |
| 5,147,307 A | 9/1992 | Gluck | |
| 5,147,631 A | 9/1992 | Glajch et al. | |
| 5,162,430 A | 11/1992 | Rhee et al. | |
| 5,163,896 A | 11/1992 | Suthanthiran et al. | |
| 5,195,540 A | 3/1993 | Shiber | |
| 5,199,441 A | 4/1993 | Hogle | |
| 5,219,339 A | 6/1993 | Saito | |
| 5,221,269 A | 6/1993 | Miller et al. | |
| 5,231,615 A | 7/1993 | Endoh | |
| 5,236,410 A | 8/1993 | Granov et al. | |
| 5,242,759 A | 9/1993 | Hall | |
| 5,250,026 A | 10/1993 | Ehrlich et al. | |
| 5,271,961 A | 12/1993 | Mathiowitz et al. | |
| 5,273,532 A | 12/1993 | Niezink et al. | |
| 5,280,788 A | 1/1994 | Janes et al. | |
| 5,281,197 A | 1/1994 | Arias et al. | |
| 5,281,408 A | 1/1994 | Unger | |
| 5,282,781 A | 2/1994 | Liprie | |
| 5,284,479 A | 2/1994 | de Jong | |
| 5,289,831 A | 3/1994 | Bosley | |
| 5,320,613 A | 6/1994 | Houge et al. | |
| 5,328,955 A | 7/1994 | Rhee et al. | |
| 5,334,381 A | 8/1994 | Unger | |
| 5,353,804 A | 10/1994 | Kornberg et al. | |
| 5,354,623 A | 10/1994 | Hall | |
| 5,366,756 A | 11/1994 | Chesterfield et al. | |
| 5,368,030 A | 11/1994 | Zinreich et al. | |
| 5,388,588 A | 2/1995 | Nabai et al. | |
| 5,394,875 A | 3/1995 | Lewis et al. | |
| 5,395,319 A | 3/1995 | Hirsch et al. | |
| 5,409,004 A | 4/1995 | Sloan | |
| 5,417,708 A | 5/1995 | Hall et al. | |
| 5,422,730 A | 6/1995 | Barlow et al. | |
| 5,425,366 A | 6/1995 | Reinhardt et al. | |
| 5,433,204 A | 7/1995 | Olson | |
| 5,449,560 A | 9/1995 | Antheunis et al. | |
| 5,451,406 A | 9/1995 | Lawin et al. | |
| 5,460,182 A | 10/1995 | Goodman et al. | |
| 5,469,847 A | 11/1995 | Zinreich et al. | |
| 5,475,052 A | 12/1995 | Rhee et al. | |
| 5,490,521 A | 2/1996 | Davis et al. | |
| 5,494,030 A | 2/1996 | Swartz et al. | |
| 5,499,989 A | 3/1996 | LaBash | |
| 5,507,807 A | 4/1996 | Shippert | |
| 5,508,021 A | 4/1996 | Grinstaff et al. | |
| 5,514,085 A | 5/1996 | Yoon | |
| 5,522,896 A | 6/1996 | Prescott | |
| 5,538,726 A | 7/1996 | Order | |
| 5,542,915 A | 8/1996 | Edwards et al. | |
| 5,549,560 A | 8/1996 | Van de Wijdeven | |
| RE35,391 E | 12/1996 | Brauman | |
| 5,580,568 A | 12/1996 | Greff et al. | |
| 5,585,112 A | 12/1996 | Unger et al. | |
| 5,611,352 A | 3/1997 | Kobren et al. | |
| 5,626,611 A | 5/1997 | Liu et al. | |
| 5,628,781 A | 5/1997 | Williams et al. | |
| 5,629,008 A | 5/1997 | Lee | |
| 5,636,255 A | 6/1997 | Ellis | |
| 5,643,246 A | 7/1997 | Leeb et al. | |
| 5,646,146 A | 7/1997 | Faarup et al. | |
| 5,667,767 A | 9/1997 | Greff et al. | |
| 5,673,841 A | 10/1997 | Schulze et al. | |
| 5,676,146 A | 10/1997 | Scarborough | |
| 5,676,925 A | 10/1997 | Klaveness et al. | |
| 5,688,490 A | 11/1997 | Tournier et al. | |
| 5,690,120 A | 11/1997 | Jacobsen et al. | |
| 5,695,480 A | 12/1997 | Evans et al. | |
| 5,702,128 A | 12/1997 | Maxim et al. | |
| 5,702,716 A | 12/1997 | Dunn et al. | |
| 5,747,060 A | 5/1998 | Sackler et al. | |
| 5,762,903 A | 6/1998 | Park et al. | |
| 5,769,086 A | 6/1998 | Ritchart et al. | |
| 5,776,496 A | 7/1998 | Violante et al. | |
| 5,779,647 A | 7/1998 | Chau et al. | |
| 5,782,764 A | 7/1998 | Werne | |
| 5,782,775 A | 7/1998 | Milliman et al. | |
| 5,795,308 A | 8/1998 | Russin | |
| 5,800,362 A | 9/1998 | Kobren et al. | |
| 5,800,389 A | 9/1998 | Burney et al. | |
| 5,800,445 A | 9/1998 | Ratcliff et al. | |
| 5,800,541 A | 9/1998 | Rhee et al. | |
| 5,817,022 A | 10/1998 | Vesely | |
| 5,820,918 A | 10/1998 | Ronan et al. | |
| 5,821,184 A | 10/1998 | Haines et al. | |
| 5,823,198 A | 10/1998 | Jones et al. | |
| 5,824,042 A | 10/1998 | Lombardi et al. | |
| 5,824,081 A | 10/1998 | Knapp et al. | |
| 5,830,178 A | 11/1998 | Jones et al. | |
| 5,842,477 A | 12/1998 | Naughton et al. | |
| 5,842,999 A | 12/1998 | Pruitt et al. | |
| 5,845,646 A | 12/1998 | Lemelson | |
| 5,846,220 A | 12/1998 | Elsberry | |
| 5,851,508 A | 12/1998 | Greff et al. | |
| 5,853,366 A | 12/1998 | Dowlatshahi | |
| 5,865,806 A | 2/1999 | Howell | |
| 5,869,080 A | 2/1999 | McGregor et al. | |
| 5,876,340 A | 3/1999 | Tu et al. | |

| | | | | | | |
|---|---|---|---|---|---|---|
| 5,879,357 A | 3/1999 | Heaton et al. | | 6,405,733 B1 | 6/2002 | Fogarty et al. |
| 5,891,558 A | 4/1999 | Bell et al. | | 6,409,742 B1 | 6/2002 | Fulton, III et al. |
| 5,897,507 A | 4/1999 | Kortenbach et al. | | 6,424,857 B1 | 7/2002 | Henrichs et al. |
| 5,902,310 A | 5/1999 | Foerster et al. | | 6,425,903 B1 | 7/2002 | Voegele |
| 5,911,705 A | 6/1999 | Howell | | 6,427,081 B1 | 7/2002 | Burbank et al. |
| 5,921,933 A | 7/1999 | Sarkis et al. | | 6,450,937 B1 | 9/2002 | Mercereau et al. |
| 5,922,024 A | 7/1999 | Janzen et al. | | 6,450,938 B1 | 9/2002 | Miller |
| 5,928,626 A | 7/1999 | Klaveness et al. | | 6,471,700 B1 | 10/2002 | Burbank et al. |
| 5,928,773 A | 7/1999 | Andersen | | 6,478,790 B2 | 11/2002 | Bardani |
| 5,941,890 A | 8/1999 | Voegele et al. | | 6,506,156 B1 | 1/2003 | Jones et al. |
| 5,942,209 A | 8/1999 | Leavitt et al. | | 6,511,468 B1 | 1/2003 | Cragg et al. |
| 5,948,425 A | 9/1999 | Janzen et al. | | 6,537,193 B1 | 3/2003 | Lennox |
| 5,954,670 A | 9/1999 | Baker | | 6,540,981 B2 | 4/2003 | Klaveness et al. |
| 5,972,817 A | 10/1999 | Haines et al. | | 6,544,185 B2 | 4/2003 | Montegrande |
| 5,989,265 A | 11/1999 | Bouquet De La Joliniere et al. | | 6,551,253 B2 | 4/2003 | Worm et al. |
| 6,015,541 A | 1/2000 | Greff et al. | | 6,554,760 B2 | 4/2003 | Lamoureux et al. |
| 6,030,333 A | 2/2000 | Sioshansi et al. | | 6,562,317 B2 | 5/2003 | Greff et al. |
| 6,053,925 A | 4/2000 | Barnhart | | 6,564,806 B1 | 5/2003 | Fogarty et al. |
| 6,056,700 A | 5/2000 | Burney et al. | | 6,565,551 B1 | 5/2003 | Jones et al. |
| 6,066,122 A | 5/2000 | Fisher | | 6,567,689 B2 | 5/2003 | Burbank et al. |
| 6,066,325 A | 5/2000 | Wallace et al. | | 6,575,888 B2 | 6/2003 | Zamora et al. |
| 6,071,301 A | 6/2000 | Cragg et al. | | 6,575,991 B1 | 6/2003 | Chesbrough et al. |
| 6,071,310 A | 6/2000 | Picha et al. | | 6,605,047 B2 | 8/2003 | Zarins et al. |
| 6,071,496 A | 6/2000 | Stein et al. | | 6,610,026 B2 | 8/2003 | Cragg et al. |
| 6,096,065 A | 8/2000 | Crowley | | 6,613,002 B1 | 9/2003 | Clark et al. |
| 6,096,070 A | 8/2000 | Ragheb et al. | | 6,616,630 B1 | 9/2003 | Woehr et al. |
| 6,106,473 A | 8/2000 | Violante et al. | | 6,626,850 B1 | 9/2003 | Chau et al. |
| 6,117,108 A | 9/2000 | Woehr et al. | | 6,628,982 B1 | 9/2003 | Thomas et al. |
| 6,120,536 A | 9/2000 | Ding et al. | | 6,636,758 B2 | 10/2003 | Sanchez et al. |
| 6,142,955 A | 11/2000 | Farascioni et al. | | 6,638,234 B2 | 10/2003 | Burbank et al. |
| 6,159,445 A | 12/2000 | Klaveness et al. | | 6,638,308 B2 | 10/2003 | Corbitt, Jr. et al. |
| 6,161,034 A | 12/2000 | Burbank et al. | | 6,652,442 B2 | 11/2003 | Gatto |
| 6,162,192 A | 12/2000 | Cragg et al. | | 6,656,192 B2 | 12/2003 | Espositio et al. |
| 6,174,330 B1 | 1/2001 | Stinson | | 6,662,041 B2 | 12/2003 | Burbank et al. |
| 6,177,062 B1 | 1/2001 | Stein et al. | | 6,699,205 B2 | 3/2004 | Fulton, III et al. |
| 6,181,960 B1 | 1/2001 | Jensen et al. | | 6,712,774 B2 | 3/2004 | Voegele et al. |
| 6,183,497 B1 | 2/2001 | Sing et al. | | 6,712,836 B1 | 3/2004 | Berg et al. |
| 6,190,350 B1 | 2/2001 | Davis et al. | | 6,716,444 B1 | 4/2004 | Castro et al. |
| 6,200,258 B1 | 3/2001 | Slater et al. | | 6,725,083 B1 | 4/2004 | Burbank et al. |
| 6,203,524 B1 | 3/2001 | Burney et al. | | 6,730,042 B2 | 5/2004 | Fulton et al. |
| 6,203,568 B1 | 3/2001 | Lombardi et al. | | 6,730,044 B2 | 5/2004 | Stephens et al. |
| 6,213,957 B1 | 4/2001 | Milliman et al. | | 6,746,661 B2 | 6/2004 | Kaplan |
| 6,214,045 B1 | 4/2001 | Corbitt, Jr. et al. | | 6,746,773 B2 | 6/2004 | Llanos et al. |
| 6,214,315 B1 | 4/2001 | Greff et al. | | 6,752,154 B2 | 6/2004 | Fogarty et al. |
| 6,220,248 B1 | 4/2001 | Voegele et al. | | 6,766,186 B1 | 7/2004 | Hoyns et al. |
| 6,224,630 B1 | 5/2001 | Bao et al. | | 6,774,278 B1 | 8/2004 | Ragheb et al. |
| 6,228,049 B1 | 5/2001 | Schroeder et al. | | 6,780,179 B2 | 8/2004 | Lee et al. |
| 6,228,055 B1 | 5/2001 | Foerster et al. | | 6,824,507 B2 | 11/2004 | Miller |
| 6,231,615 B1 | 5/2001 | Preissman | | 6,824,527 B2 | 11/2004 | Gollobin |
| 6,234,177 B1 | 5/2001 | Barsch | | 6,846,320 B2 | 1/2005 | Ashby et al. |
| 6,241,687 B1 | 6/2001 | Voegele et al. | | 6,862,470 B2 | 3/2005 | Burbank et al. |
| 6,241,734 B1 | 6/2001 | Scribner et al. | | 6,863,685 B2 | 3/2005 | Davila et al. |
| 6,251,418 B1 | 6/2001 | Ahern et al. | | 6,899,731 B2 | 5/2005 | Li et al. |
| 6,261,243 B1 | 7/2001 | Burney et al. | | 6,918,927 B2 | 7/2005 | Bates et al. |
| 6,261,302 B1 | 7/2001 | Voegele et al. | | 6,936,014 B2 | 8/2005 | Vetter et al. |
| 6,264,917 B1 | 7/2001 | Klaveness et al. | | 6,939,318 B2 | 9/2005 | Stenzel |
| 6,270,464 B1 | 8/2001 | Fulton, III et al. | | 6,945,973 B2 | 9/2005 | Bray |
| 6,270,472 B1 * | 8/2001 | Antaki et al. ............ 604/61 | | 6,951,564 B2 | 10/2005 | Espositio et al. |
| 6,287,278 B1 | 9/2001 | Woehr et al. | | 6,994,712 B1 | 2/2006 | Fisher et al. |
| 6,287,332 B1 | 9/2001 | Bolz et al. | | 7,001,341 B2 | 2/2006 | Gellman et al. |
| 6,289,229 B1 | 9/2001 | Crowley | | 7,008,382 B2 | 3/2006 | Adams et al. |
| 6,312,429 B1 | 11/2001 | Burbank et al. | | 7,014,610 B2 | 3/2006 | Koulik |
| 6,316,522 B1 | 11/2001 | Loomis et al. | | 7,025,765 B2 | 4/2006 | Balbierz et al. |
| 6,335,029 B1 | 1/2002 | Kamath et al. | | 7,044,957 B2 | 5/2006 | Foerster et al. |
| 6,336,904 B1 | 1/2002 | Nikolchev | | 7,083,576 B2 | 8/2006 | Zarins et al. |
| 6,340,367 B1 | 1/2002 | Stinson et al. | | 7,125,397 B2 | 10/2006 | Woehr et al. |
| 6,343,227 B1 | 1/2002 | Crowley | | 7,172,549 B2 | 2/2007 | Slater et al. |
| 6,347,240 B1 | 2/2002 | Foley et al. | | 7,214,211 B2 | 5/2007 | Woehr et al. |
| 6,347,241 B2 | 2/2002 | Burbank et al. | | 7,229,417 B2 | 6/2007 | Foerster et al. |
| 6,350,244 B1 | 2/2002 | Fisher | | 7,236,816 B2 | 6/2007 | Kumar et al. |
| 6,350,274 B1 | 2/2002 | Li | | 7,264,613 B2 | 9/2007 | Woehr et al. |
| 6,354,989 B1 | 3/2002 | Nudeshima | | 7,294,118 B2 | 11/2007 | Saulenas et al. |
| 6,356,112 B1 | 3/2002 | Tran et al. | | 7,297,725 B2 | 11/2007 | Winterton et al. |
| 6,356,782 B1 | 3/2002 | Sirimanne et al. | | 7,329,402 B2 | 2/2008 | Unger et al. |
| 6,358,217 B1 | 3/2002 | Bourassa | | 7,416,533 B2 | 8/2008 | Gellman et al. |
| 6,363,940 B1 | 4/2002 | Krag | | 7,424,320 B2 | 9/2008 | Chesbrough et al. |
| 6,371,904 B1 | 4/2002 | Sirimanne et al. | | 7,449,000 B2 | 11/2008 | Adams et al. |
| 6,394,965 B1 | 5/2002 | Klein | | 7,527,610 B2 | 5/2009 | Erickson |
| 6,403,758 B1 | 6/2002 | Loomis | | 7,569,065 B2 | 8/2009 | Chesbrough et al. |

| | | |
|---|---|---|
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,819,820 B2 | 10/2010 | Field et al. |
| 2001/0003791 A1 | 6/2001 | Burbank et al. |
| 2001/0006616 A1 | 7/2001 | Leavitt et al. |
| 2001/0033867 A1 | 10/2001 | Ahern et al. |
| 2001/0049481 A1 | 12/2001 | Fulton, III et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0038087 A1 | 3/2002 | Forcier et al. |
| 2002/0045842 A1 | 4/2002 | Van Bladel et al. |
| 2002/0049411 A1 | 4/2002 | Lamoureux et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0188196 A1 | 12/2002 | Burbank et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0106891 A1 | 6/2004 | Langan et al. |
| 2004/0116802 A1 | 6/2004 | Jessop et al. |
| 2004/0116806 A1 | 6/2004 | Burbank et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0167619 A1 | 8/2004 | Case et al. |
| 2004/0193044 A1 | 9/2004 | Burbank et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236211 A1 | 11/2004 | Burbank et al. |
| 2004/0236212 A1 | 11/2004 | Lubock et al. |
| 2004/0236213 A1 | 11/2004 | Jones et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0063908 A1 | 3/2005 | Burbank et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0143656 A1 | 6/2005 | Burbank et al. |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2007/0021642 A1 | 1/2007 | Lamoureux et al. |
| 2007/0038145 A1 | 2/2007 | Field |
| 2007/0083132 A1 | 4/2007 | Sharrow |
| 2007/0087026 A1 | 4/2007 | Field |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0093714 A1 | 4/2009 | Chesbrough et al. |
| 2009/0131825 A1 | 5/2009 | Burbank et al. |
| 2010/0010341 A1 | 1/2010 | Talpade et al. |
| 2010/0030072 A1 | 2/2010 | Casanova et al. |
| 2010/0030149 A1 | 2/2010 | Carr, Jr. |
| 2011/0028836 A1 | 2/2011 | Ranpura |

FOREIGN PATENT DOCUMENTS

| | | |
|---|---|---|
| EP | 0 146 699 | 9/1984 |
| EP | 0 255 123 | 2/1988 |
| EP | 0 292 936 | 11/1988 |
| EP | 0 481 685 A1 | 10/1991 |
| EP | 0 458 745 A1 | 11/1991 |
| EP | 0475077 A2 | 3/1992 |
| EP | 0 552 924 | 7/1993 |
| EP | 0769281 A2 | 4/1997 |
| EP | 1114618 A2 | 1/2001 |
| EP | 1163888 A1 | 12/2001 |
| EP | 1 216 721 | 6/2002 |
| EP | 1281416 A2 | 6/2002 |
| EP | 1364628 A1 | 11/2003 |
| EP | 1 493 451 | 1/2005 |
| EP | 1767167 A2 | 3/2007 |
| EP | 0 386 936 | 9/2010 |
| FR | 2646674 A3 | 11/1990 |
| GB | 708 148 | 4/1954 |
| JP | 2131757 A | 5/1990 |
| WO | 8906978 A1 | 8/1989 |
| WO | WO 91/12823 | 9/1991 |
| WO | WO 93/14712 | 5/1993 |
| WO | 9317671 A1 | 9/1993 |
| WO | WO 93/17718 | 9/1993 |

| | | | |
|---|---|---|---|
| WO | 9416647 A1 | 8/1994 |
| WO | 9507057 A1 | 3/1995 |
| WO | WO 96/08208 | 3/1996 |
| WO | WO 98/06346 | 2/1998 |
| WO | 9908607 A1 | 2/1999 |
| WO | WO 99/30764 | 6/1999 |
| WO | 9935966 A1 | 7/1999 |
| WO | 9951143 A1 | 10/1999 |
| WO | 0023124 A1 | 4/2000 |
| WO | 0028554 A1 | 5/2000 |
| WO | WO 00/24332 | 5/2000 |
| WO | WO 00/38579 | 7/2000 |
| WO | 0054689 A1 | 9/2000 |
| WO | WO 01/08578 | 2/2001 |
| WO | 0170114 A1 | 9/2001 |
| WO | 0207786 A2 | 1/2002 |
| WO | 0241786 A2 | 5/2002 |
| WO | 03000308 A1 | 1/2003 |
| WO | 2004045444 A2 | 6/2004 |
| WO | WO 2004/105626 | 12/2004 |
| WO | 2005013832 A1 | 2/2005 |
| WO | WO 2005/039446 | 5/2005 |
| WO | WO 2005/089664 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Fucci, V., et al., "Large Bowel Transit Times Using Radiopaque Markers in Normal Cats", *J. of Am. Animal Hospital Assn.*, Nov.-Dec. 1995 31 (6) 473-477.

Schindlbeck, N.E., et al., "Measurement of Colon Transit Time", *J. of Gastroenterology*, No. 28, pp. 399-404, 1990.

Shiga et al., Preparation of Poly(D, L-lactide) and Copoly(lactide-glycolide) Microspheres of Uniform Size, *J. Pharm. Pharmacol.* 1996 48:891-895.

Eiselt, P. et al, "Development of Technologies Aiding Large—Tissue Engineering", Biotechnol. Prog., vol. 14, No. 1, pp. 134-140, 1998.

Johnson & Johnson: Breast Biopsy (minimally invasive): Surgical Technique: Steps in the Mamotome Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

Press release for Biopsys Ethicon Endo-Surgery (Europe) GmbH; The Mammotome Vacuum Biopsy System. From: http://www.medicine-news.com/articles/devices/mammotome.html. 3 pages.

* cited by examiner

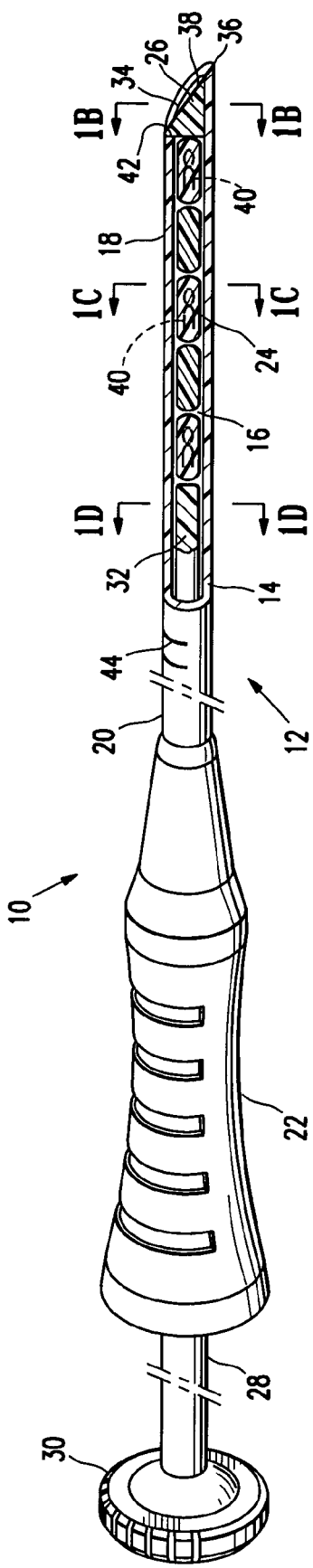
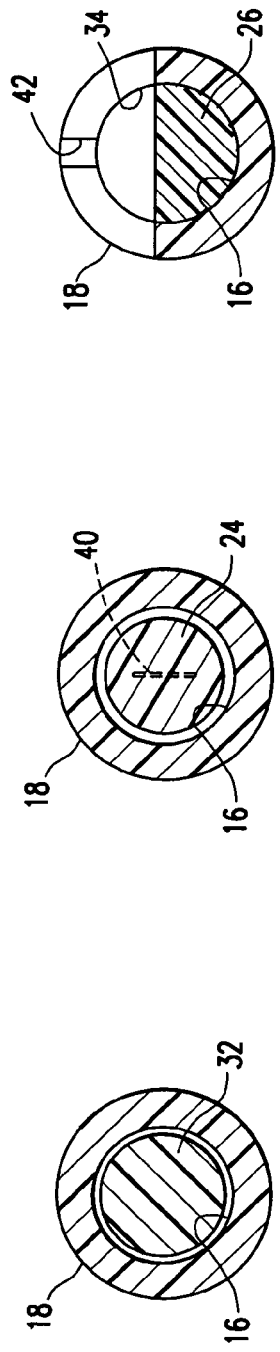
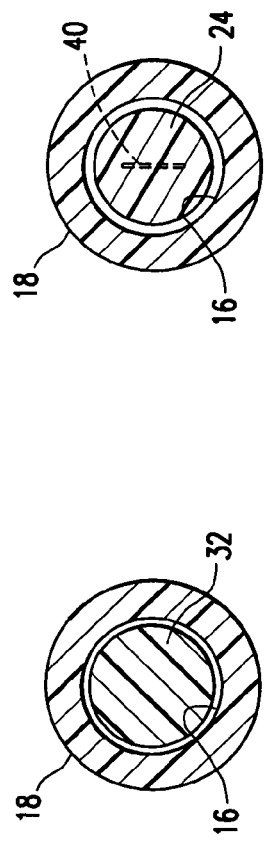
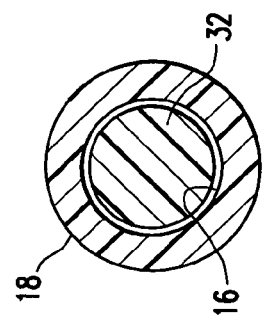
FIG. 1A
FIG. 1B
FIG. 1C
FIG. 1D

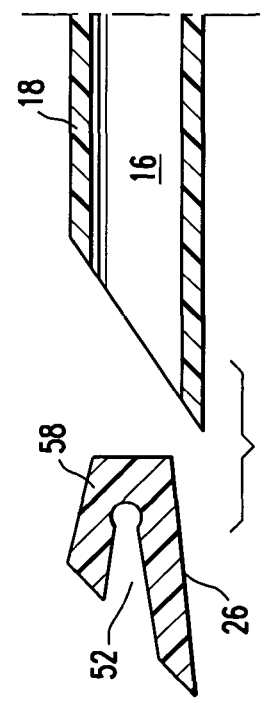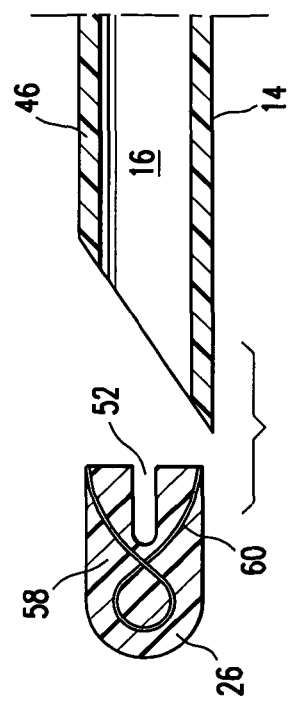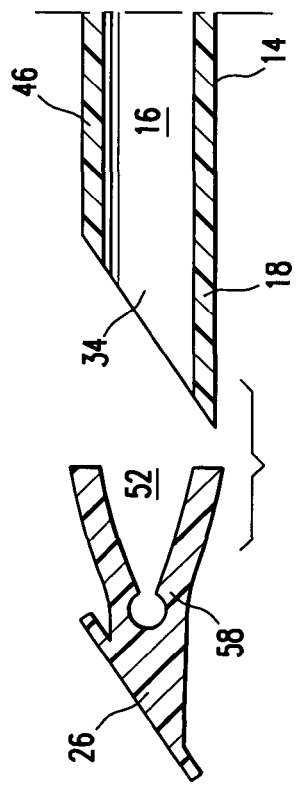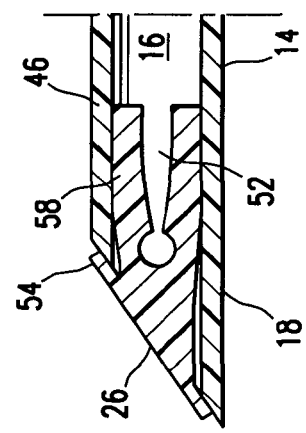

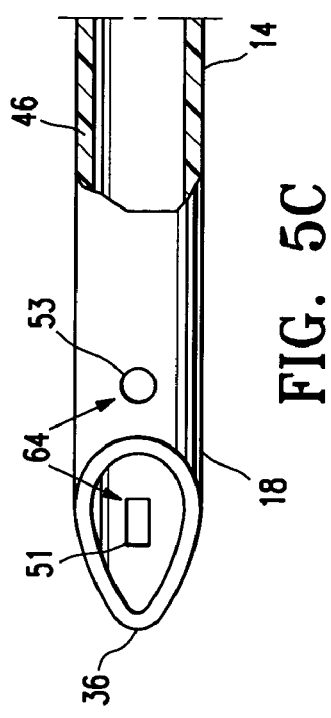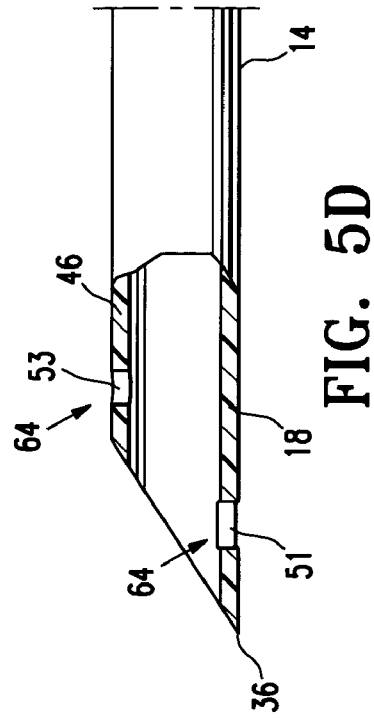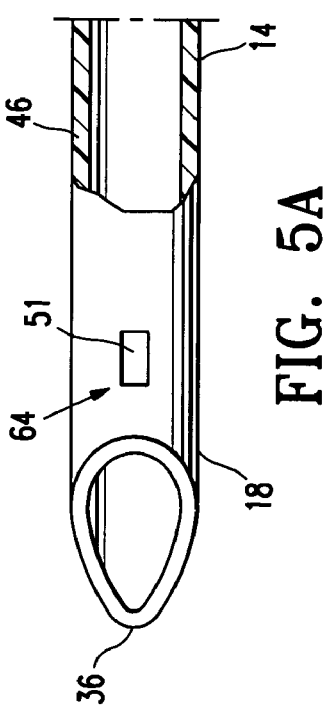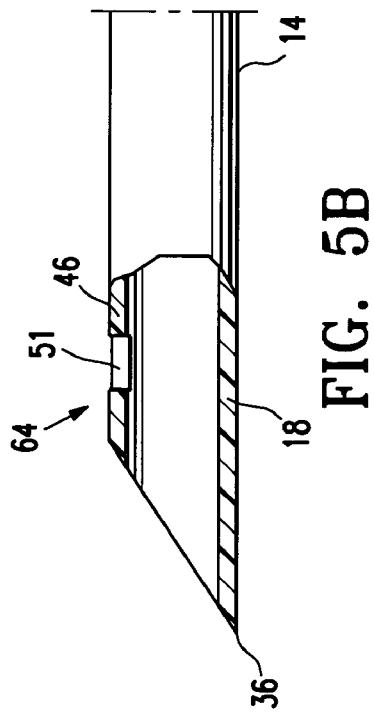

PLUGGED TIP DELIVERY TUBE FOR MARKER PLACEMENT

RELATED APPLICATIONS

This application is a continuation of application Ser. No. 10/174,401, filed Jun. 17, 2002, now U.S. Pat. No. 7,651,505, which is incorporated by reference herein in its entirety and from which priority is claimed.

FIELD OF THE INVENTION

The invention is directed generally to devices and methods for delivering markers to a desired location within a patient's body. In particular, the invention is directed to devices, assemblies, and methods configured to retain a biological marker within a delivery device before delivery of the marker to a desired intracorporeal location.

BACKGROUND OF THE INVENTION

In diagnosing and treating certain medical conditions, it is often desirable to mark a suspicious body site for the subsequent taking of a biopsy, delivery of medicine, radiation, or other treatment, to mark a location from which a biopsy was taken, or at which some other procedure was performed. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a therapeutic plan for the appropriate surgical procedure or other course of treatment.

In many instances, the suspicious tissue to be sampled is located in a subcutaneous site, such as inside a human breast. To minimize surgical intrusion into patient's body, it is often desirable to insert a small instrument, such as a biopsy needle, into the body for extracting the biopsy specimen while imaging the procedure using fluoroscopy, ultrasonic imaging, x-rays, magnetic resonance imaging (MRI) or any other suitable form of imaging technique. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

Periodic physical examination of the breasts and mammography are important for early detection of potentially cancerous lesions. In mammography, the breast is compressed between two plates while specialized x-ray images are taken. If an abnormal mass in the breast is found by physical examination or mammography, ultrasound may be used to determine whether the mass is a solid tumor or a fluid-filled cyst. Solid masses are usually subjected to some type of tissue biopsy to determine if the mass is cancerous.

If a solid mass or lesion is large enough to be palpable, a tissue specimen can be removed from the mass by a variety of techniques, including but not limited to open surgical biopsy, a technique known as Fine Needle Aspiration Biopsy (FNAB) and instruments characterized as "vacuum assisted large core biopsy devices".

If a solid mass of the breast is small and non-palpable (e.g., the type typically discovered through mammography), a biopsy procedure known as stereotactic needle biopsy may be used. In performing a stereotactic needle biopsy of a breast, the patient lies on a special biopsy table with her breast compressed between the plates of a mammography apparatus and two separate x-rays or digital video views are taken from two different points of view. A computer calculates the exact position of the lesion as well as depth of the lesion within the breast. Thereafter, a mechanical stereotactic apparatus is programmed with the coordinates and depth information calculated by the computer, and such apparatus is used to precisely advance the biopsy needle into the small lesion. Depending on the type of biopsy needle(s) used, this stereotactic technique may be used to obtain cytologic specimens, e.g., obtained through FNAB or it may be used to obtain histologic specimens e.g., obtained through coring needle biopsy. Usually at least five separate biopsy specimens are obtained from locations around the small lesion as well as one from the center of the lesion.

The available treatment options for cancerous lesions of the breast include various degrees of mastectomy or lumpectomy and radiation therapy, as well as chemotherapy and combinations of these treatments. However, radiographically visible tissue features, originally observed in a mammogram, may be removed, altered or obscured by the biopsy procedure, and may heal or otherwise become altered following the biopsy. In order for the surgeon or radiation oncologist to direct surgical or radiation treatment to the precise location of the breast lesion several days or weeks after the biopsy procedure was performed, it is desirable that a biopsy site marker be placed in or on the patient's body to serve as a landmark for subsequent location of the lesion site. A biopsy site marker may be a permanent marker (e.g., a metal marker visible under X-ray examination), or a temporary marker (e.g., a bioresorbable marker detectable with ultrasound). While current radiographic type markers may persist at the biopsy site, an additional mammography generally must be performed at the time of follow up treatment or surgery in order to locate the site of the previous surgery or biopsy. In addition, once the site of the previous procedure is located using mammography, the site must usually be marked with a location wire which has a hook on the end which is advanced into site of the previous procedure. The hook is meant to fix the tip of the location wire with respect to the site of the previous procedure so that the patient can then be removed from the confinement of the mammography apparatus and the follow-up procedure performed. However, as the patient is removed from the mammography apparatus, or otherwise transported the position of the location wire can change or shift in relation to the site of the previous procedure. This, in turn, can result in follow-up treatments being misdirected to an undesired portion of the patient's tissue.

As an alternative or adjunct to radiographic imaging, ultrasonic imaging and visualization techniques (herein abbreviated as "USI") can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are visible using USI. Such a marker enables a follow-up procedure to be performed without the need for traditional radiographic mammography imaging which, as discussed above, can be subject to inaccuracies as a result of shifting of the location wire as well as being tedious and uncomfortable for the patient.

Placement of a marker or multiple markers at a location within a patient's body requires delivery devices capable of holding markers within the device until the device is properly situated within a breast or other body location. Accordingly, devices and methods for retaining markers within a marker delivery device while allowing their expulsion from the devices at desired intracorporeal locations are desired.

SUMMARY OF THE INVENTION

The invention provides devices and systems for delivery of markers to a site within a patient's body. Delivery systems embodying features of the invention include a marker delivery tube with a removable plug. Plugs embodying features of the invention are held within an orifice at the tip of the delivery tube, retaining markers within the delivery tube, until it is desired that the markers be ejected. The plug may then be ejected or removed from the orifice, allowing the delivery of the markers to a desired site within a patient's body. Plugs and delivery tubes embodying features of the invention may have retaining features, such as recesses or protuberances, configured to releasably retain a plug within a delivery tube until ejection of the plug from the delivery tube is desired. The retaining features are typically complementary pairs, such as a plug protuberance configured to fit into a recess in the delivery tube.

Assemblies embodying features of the invention include marker delivery devices having a delivery tube with an orifice at its distal tip, an inner bore leading to an orifice, and at least one marker (preferably more than one) within the bore of the delivery tube. A plug is disposed at least in part within the bore and orifice to prevent markers from prematurely passing through the orifice and to prevent tissue from entering the bore when the delivery tube is advanced through tissue. The plug may itself serve as a marker, and may be the sole marker, although typically the delivery tube contains a plug and at least one other marker. The plug is releasably secured within or adjacent to the orifice in order to retain a marker within the delivery tube bore proximate thereto but to allow passage of the marker out of the orifice when the plug is ejected from the orifice. The plug may partially or completely occlude the orifice, and is configured to retain the marker within the delivery tube before the marker is to be placed at a desired location within a patient's body, and to allow the marker to pass out of the orifice when delivery of the marker is desired. A movable plunger may be slidably disposed within the tube from an initial position accommodating the marker or markers and the plug within the tube, to a delivery position to push a marker against the plug to push the plug out of the orifice and to then eject one or more markers through the orifice.

The plug is preferably configured to be releasably retained within the delivery tube, and may be aligned in a preferred orientation within the delivery tube, to properly orient an inclined face within the orifice. A plug may be configured to fit tightly within a part of the bore of a delivery device so as to be retained by pressure; may have a portion configured to contact a slot, hole, notch, ridge, tab, lip, or other feature of a delivery tube; may be configured to be retained by a tab; may include an internal retention element, such as a coil, a spring, a clip, a loop, an arch, or a resilient core, that is configured to press an outer portion of a plug against a delivery tube wall or to contact a retaining feature such as a tab, slot, notch or hole; may be pressed against at least part of the bore of a delivery tube by an external retention element such as a pin, wedge, clip, spring, coil or other element applied to a plug; or by otherwise engaging a portion of a delivery tube effective to be releasably retained within a delivery tube.

The plug is preferably biocompatible, and may itself be a marker that is detectable within a patient's body visually, tactilely, by imaging (including ultrasound, radiographic, magnetic resonance, or other form of imaging), or is otherwise detectable. A plug may be a bio-resorbable temporary marker made up of bio-resorbable materials, or may be a permanent marker including non-bio-resorbable materials as well. A plug may also include bio-active materials (e.g., hemostatic materials, anesthetic materials, absorbent materials, antibiotic materials, antifungal materials, antiviral materials, chemotherapeutic materials, radioactive materials, and other pharmaceutical materials) as well as biologically inert materials.

Systems and devices embodying features of the invention may have markings or indicators to aid in placement of the delivery tube in a desired location. In addition, methods of using systems and devices embodying features of the invention include guiding the insertion of the delivery tube with the aid of an imaging device, such as an ultrasound imaging device, an x-ray imaging device, and a magnetic resonance imaging device, which may be used to image the plug, a marker retained within the delivery device, a portion of the delivery device, or combinations of these.

The invention provides the advantages of securely retaining markers within a marker delivery device, improving accuracy and avoiding errors in of placement of markers at desired locations within a patient's body, preventing ingress of tissue into the distal tip of the device when it is advanced through tissue, and guiding the device by use of an imaging device. These and other advantages of the invention will become more apparent from the following description when taken in conjunction with the accompanying drawings.

BRIEF DESCRIPTION OF THE DRAWINGS

FIG. 1A is a partly cut-away perspective view of a marker delivery assembly embodying features of the invention showing several markers within a marker delivery device and a plug embodying features of the invention occluding the tip of the delivery device.

FIG. 1B is a transverse cross-sectional view of the marker delivery assembly of FIG. 1A taken at line 1B-1B.

FIG. 1C is a transverse cross-sectional view of the marker delivery assembly of FIG. 1A taken at line 1C-1C.

FIG. 1D is a transverse cross-sectional view of the marker delivery assembly of FIG. 1A taken at line 1D-1D.

FIG. 3A is a longitudinal cross-sectional view of a compressible plug embodying features of the invention disposed outside a distal portion of a delivery tube.

FIG. 3B is a longitudinal cross-sectional view of the compressible plug of FIG. 3A embodying disposed within the distal portion of the delivery tube.

FIG. 3C is a longitudinal cross-sectional view of an alternative embodiment of a compressible plug.

FIG. 3D is a longitudinal cross-section of a plug containing an internal retention element configured to press against the wall of a delivery tube.

FIGS. 5A-5H are alternating plan and elevation views of distal portions of delivery tubes of marker delivery devices embodying features of the invention configured to retain a plug by having holes or slots through the tube wall.

DETAILED DESCRIPTION OF THE INVENTION

Figure 2C:
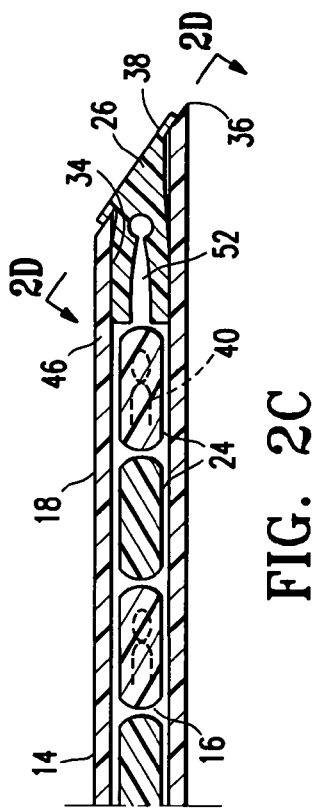
FIGS. 2A-2C and 2E-2H are longitudinal cross-sectional views of a delivery tube distal portion embodying features of the invention configured to retain a plug, containing markers and a plug embodying features of the invention.

Marker delivery assemblies embodying features of the invention are illustrated in FIGS. 1A-1D. Such assemblies include marker delivery devices, markers, and a plug occluding a distal portion of the delivery device. The assembly 10 shown in FIG. 1A includes a delivery device 12, delivery tube 14 with a bore 16, a distal portion 18, and a proximal portion 20 with a handle 22. Several markers 24, and a plug 26 are shown disposed within the bore 16. A plunger 28 with a plunger handle 30 and a plunger distal end 32 is movable within the tube bore 16, and is configured to push markers 24 and plug 26 out of orifice 34 at the distal tip 36 of delivery tube 14 when the distal end 32 of plunger 28 moves in a distal direction. Plunger handle 30 allows an operator to readily manipulate plunger 28. A device 12 may include a plunger locking mechanism to prevent inadvertent longitudinal movement of plunger 28; for example, a plunger 28 and a handle 22 may be configured so that plunger 28 must be rotated some amount before it is able to be moved in a longitudinal direction (by, e.g., having a lateral tab protruding from a portion of the plunger 28 that prevents longitudinal plunger movement until the tab is moved to a channel configured to accept it).

Plug 26 may substantially fill orifice 34, as shown in FIG. 1A, or may occupy or block only a portion of orifice 34. A plug 26 preferably does not interfere with the sharp edge of orifice 34 or pointed tip 36 of a delivery tube 14. Where distal tip 36 of delivery tube 14 is sharp, as shown in FIG. 1A, the distal surface 38 of plug 26 is preferably configured with an inclined surface to closely follow the conformation of distal tip 36 to provide more effective penetration.

Markers 24 are preferably configured to slide readily within tube bore 16. Plug 26 is configured to be releasably secured within a portion of tube bore 16, such as a distal portion 18 or orifice 34, effective to prevent inadvertent exit or release of markers 24 from delivery tube 14. The engagement of plug 26 with delivery tube 14 is further configured to be readily releasable when desired. For example, plug 26 is configured to release its engagement with delivery tube 14 effective to allow exit of markers 24 upon distal movement of plunger 28. Markers 24 are made with detectable, biocompatible materials, and may include a radiopaque element 40. Plug 26 may be made from the same or similar materials as a marker 24, and may also include a radiopaque element 40.

FIG. 1A shows a marker delivery device 12 having a delivery tube 14 with a Distal tip 36 having a notch 42 configured to retain a plug 26. A notch 42 is effective to retain a plug 26, particularly if a portion of the plug 26 is formed to engage with the notch 42, or is pressed or otherwise introduced into at least a portion of the notch 42. The delivery tube 14 also has markings 44 which aid in placement of the device in a desired location within a patient's body. The markings 44 may serve as visual landmarks for guiding an operator in placing the device, and may also be radiopaque, ultrasound-reflective, or otherwise configured to be detectable by imaging devices and imaging methods.

In FIG. 1B, the plug 26 is shown in place within tube bore 16 at the distal portion 18 of delivery tube 14. In FIG. 1C, a marker 24 with radiopaque element 40 is shown within tube bore 16 of delivery tube 14. In FIG. 1D, a portion the plunger 28 is shown in place within tube bore 16 of delivery tube 14.

Figure 2D:
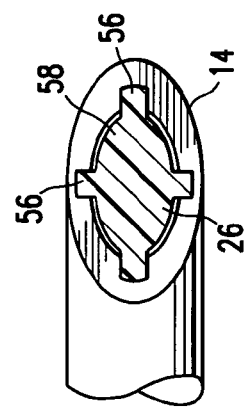
FIG. 2D is a transverse cross-sectional view of the delivery tube distal portion and plug shown in FIG. 2C.
Figure 2A:
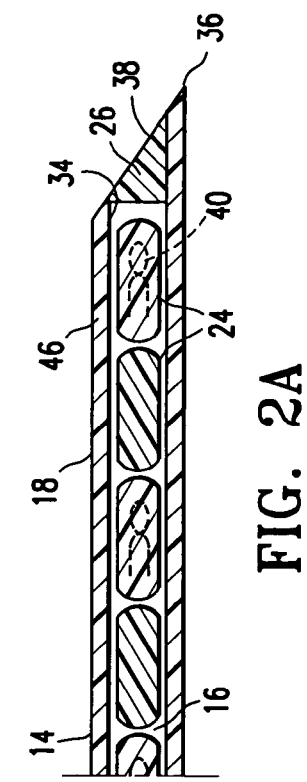

FIGS. 2A-2H illustrate several alternative embodiments of a plug 26 having features of the invention. The plugs 26 in FIGS. 2A-2C and 2E-2H are shown in longitudinal cross-section within a distal portion 18 of a delivery tube 14 of a marker delivery device 12 embodying features of the invention. FIG. 2A illustrates a plug 26 configured to be retained within a delivery tube 14 and to occlude an orifice 34. Plug 26 of FIG. 2A is configured to provide a surface 38 following a configuration generally perpendicular to wall 46 conforming to the sharp tip 36, effective to aid the penetration of sharp tip 36 into a patient's tissue as well as to retain markers 24 within a delivery device 12. A plug 26 embodying features of the invention may be retained within a delivery tube 14 effective to occlude an orifice 34 and to retain a marker 24 in any one or in more than one way. For example, a plug 26 may be retained by friction, adhesion, tension, pressure, or other mechanisms; may be retained mechanically, as by a notch, hole, slot, tab, ridge, lip or other feature of a tube 14, of the plug 26 itself, or by any combination of such elements; or by any other mechanism or method suitable to releasably retain a plug while allowing its removal at a desired time. Some examples of such features and elements are illustrated in the figures, although the devices, assemblies and elements embodying features of the invention are not limited to these examples. Any feature, element, or means of retaining a plug in a location effective to occlude an orifice 34 and to retain a marker 24 within a delivery tube 14, while allowing its removal at a desired time, is suitable for the practice of the invention.

Figure 2B:
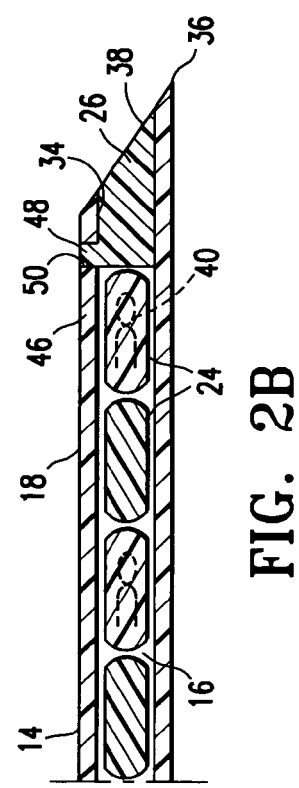

FIG. 2B illustrates a plug 26 having a protrusion 48 configured to engage a passage 50 through tube wall 46, aiding in the retention of plug 26 within bore 16 of delivery tube 14. A passage 50 may be a hole, slot, notch, or other void through a tube wall 46. Alternatively, a protrusion 48 of a plug 26 may engage a slot, notch, or crease along a bore 16 that does not completely pass through the wall 46, yet still provides purchase for retaining a plug 26 within a delivery tube 14.

FIG. 2C illustrates a plug 26 embodying features of the invention having a gap 52 allowing compression of plug 26 effective to allow insertion of plug 26 into distal portion 18, where plug 26 occludes orifice 34. Resilience of plug 26 provides outward pressure following such compression, effective to provide lateral pressure against a wall 46 of a delivery tube 14 and so to retain the plug 26 within distal portion 18 of tube 14. The embodiment of a plug 26 illustrated in FIG. 2C also has a lip portion 54 effective to limit the extent of insertion of plug 26 into delivery tube 14. It will be understood that a lip portion 54 is optional, and is not present in some plugs 26, including resilient plugs 26 embodying features of the invention. Preferably, lip portion 54 is configured to leave a sufficient amount of distal tip 36 exposed so as to not substantially interfere with penetration of sharp tip 36 into the tissue of a patient. For example, a lip portion 54 preferably comprises less than a full circumference a plug 26 having a round cross-section, and may comprise one or a few extensions 56 extending radially outwardly form a plug body 58, as illustrated in FIG. 2D in a transverse cross-sectional view of the plug 26 and tube 14 of FIG. 2C. A plug body 58 may surround a gap 52, as in the plug 26 illustrated in FIGS. 2C and 2D, or, in other embodiments, may not have a gap 52, as, e.g., in the plugs 26 illustrated in FIGS. 2A and 2B.

Figure 2E:
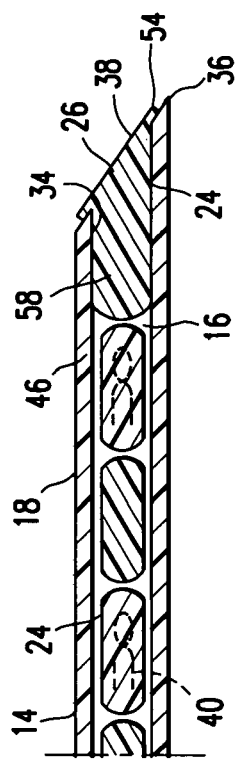

The plug 26 illustrated in FIG. 2E is an irregularly-shaped plug 26 embodying features of the invention, configured to occlude an orifice 34 and to retain markers 24 within a delivery tube 14 until the plug 26 is removed or moved away from its blocking position. An irregularly-shaped plug 26 may be put into place, for example, by the application of a liquid, flexible or pliable material that sets or hardens after placement in or around an orifice 34. Alternatively, a material may be placed in or around an orifice 34 and then treated with heat, solvent, hardener, or other treatment in order to fix the plug 26 in its final form.

Figure 2F:
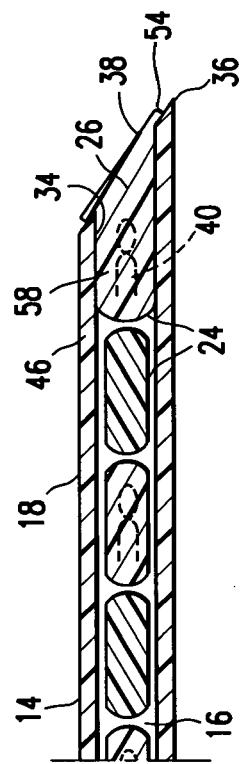

As illustrated by the embodiment of a plug 26 shown in FIG. 2F, an orifice 34 need not be completely occluded; partial occlusion of an orifice 34 by a plug 26 is sufficient to retain a marker 24 within a delivery tube 14. Such a plug 26 may be retained within the bore 16 of a delivery tube 14 by adhesion or other bonding to a tube wall 46, or by a feature of a tube 14 embodying features of the invention such as a tab, lip, hole, notch, slot, or other retaining element.

Figure 2G:
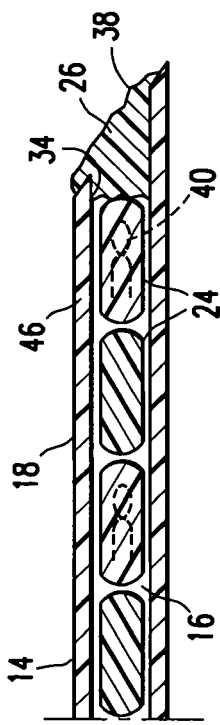
Figure 2H:
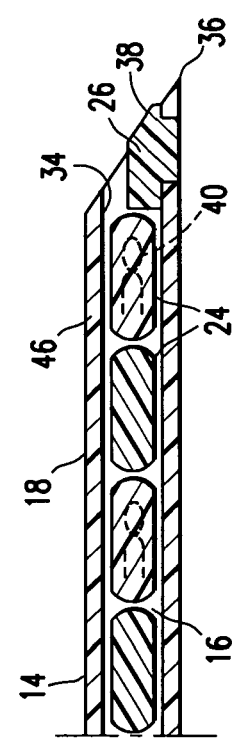

The embodiments of a plug 26 shown in FIGS. 2G and 2H include marker material effective to mark a location within a patient's body, and thus is configured to act as a marker 24 as well as a plug 26. For example, a plug 26 as illustrated in FIGS. 2G and 2H may be a plug 26 having a lip portion 54 and a body portion 58 configured to press against a tube wall 46 so as to retain plug 26 within the delivery tube 14, and including marker material so as to be able to serve as a marker 24 following ejection from orifice 34 and delivery into a desired location within a patient's body. Preferably, a lip portion 54 does not extend so far as to interfere with the cutting action of sharp tip 36. A plug 26 configured to serve as a marker 24 may include bioresorbable marker materials, and be a temporary marker, or may include non-bioresorbable marker materials, and so be a permanent marker. For example, the embodiment of a plug 26 shown in FIG. 2H is also configured to serve as a marker 24, and further includes a radiopaque element 40. Typically, a radiopaque element 40 is a permanent marker element, so that plug 26 shown in FIG. 2H, for example, may be a permanent marker.

A compressible plug 26 as illustrated in FIGS. 2C and 2D may be inserted into a delivery tube 14 through an orifice 34 as shown in FIGS. 3A and 3B. FIG. 3A shows a longitudinal cross-section of a compressible plug 26 disposed distal to an orifice 34 of a delivery tube 14. Compression of body 58 effective to reduce the size of gap 52 also reduces a lateral dimension of the plug 26 enabling a portion of the plug body 58 to be inserted through orifice 34 into tube bore 16 to be disposed in position within delivery tube 14 as shown in FIG. 3B. Resiliency of plug body 58 is effective to create pressure against a tube wall 46 so as to retain plug 26 in position within bore 16 in distal tube portion 18. In the embodiment shown in FIGS. 3A and 3B, gap 52 is disposed so as to face bore 16 of delivery tube 14. Alternatively, as shown in FIG. 3C, a gap 52 may face away from a tube bore 16. In either embodiment, plug body 58 is resiliently compressible and snugly retained within a distal tube portion 18.

In addition, a further embodiment of a plug 26 embodying features of the invention is illustrated in FIG. 3D. A plug 26 may contain an internal retention element 60 configured to press itself or a portion of a plug body 58 against a wall 46 of a delivery tube 14. Such an internal retention element 60 may be radiopaque internal retention element 60, and thus, in that case, the plug 26 will also be configured to be a radiopaque marker 24. An internal retention element 60 may be any element, including a spring, a coil, a clip, a loop, an arch, a resilient core, or other element that is configured to help retain a plug 26 within a delivery tube 14. For example, a resilient core may be a portion of a plug body 58 which includes a resilient material and which provides outward force when a plug 26 is disposed within a bore 16 of a delivery tube 14. A plug 26 as illustrated in FIG. 3D is a further example of a compressible plug 26. It will be understood that a compressible plug 26 need not have a gap 52 in order to be resiliently compressible effective to be inserted into and releasably retained within a delivery tube 14; for example, a plug 26 may be a compressible plug including an internal retention element 60, or where the entire plug body 58 is formed of a resilient material, such as, for example, a foam or spongy material which tends to re-expand after compression, or which tends to resist compression by exerting counteracting force against compression.

Figure 4A:
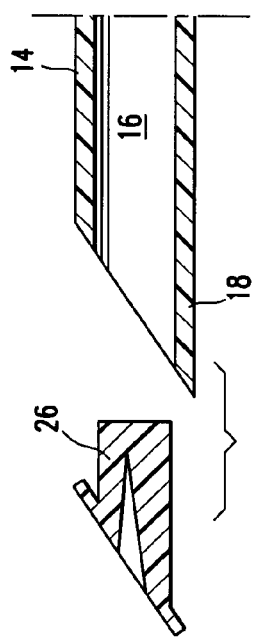
FIG. 4A is a longitudinal cross-sectional view of a plug embodying features of the invention disposed outside a distal portion of a delivery tube.
Figure 4B:
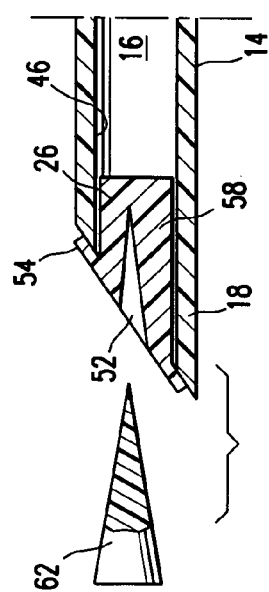
FIG. 4B is a longitudinal cross-sectional view of an external retention element and of a plug embodying features of the invention disposed within a distal portion of a delivery tube.
Figure 4C:
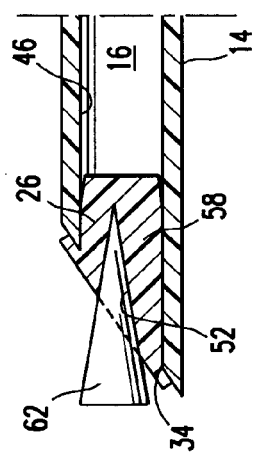
FIG. 4C is a longitudinal cross-sectional view of the external retention element inserted into the plug of FIG. 4B embodying disposed within the distal portion of the delivery tube.

A plug 26 may be releasably retained within a bore 16 of a delivery tube 14 upon addition or insertion of an external retention element 62. FIG. 4A illustrates a plug 26 embodying features of the invention disposed distal to a distal portion 18 of a delivery tube 14. FIG. 4B illustrates the plug 26 of FIG. 4A disposed within distal portion 18, in which plug body 58 does not tightly contact a tube wall 46 and plug 26 is not snugly held within delivery tube 14. Also shown in FIG. 4B is an external retention element 62 in the form of a conical pin. FIG. 4C illustrates a plug 26 embodying features of the invention including external retention element 62 mounted in a gap 52. Following insertion of external retention element 62 into plug 26, at least a portion of plug body 58 contacts tube wall 46 effective to releasably retain plug 26 within a distal portion 18 of delivery tube 14 effective to occlude orifice 34 and to retain a marker 24. In other embodiments, an external retention element 62 may be a wedge, a screw, a mandrel, or any other element configured to tend to expand a portion of a plug body 58 effective to exert force against a tube wall 46, such as by tending to expand a plug body 58, or otherwise to aid in retaining a plug 26 within a distal portion 18 of a delivery tube 14.

Figure 4D:
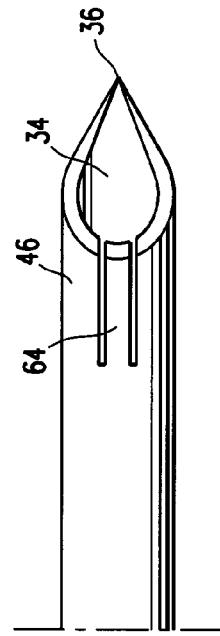
FIG. 4D is a perspective view of a sharp tip of a delivery tube distal portion embodying features of the invention having slits forming a tab configured to retain and align a plug.
Figure 4E:
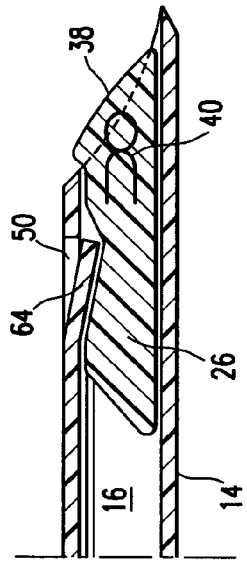
FIG. 4E is a longitudinal cross-section of a delivery tube distal portion embodying features of the invention having a tab configured to retain a plug, and containing a plug configured to be retained and aligned by a tab.
Figure 4F:
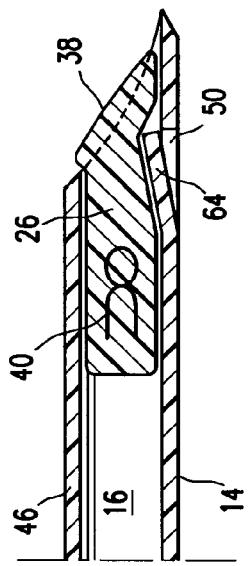
FIG. 4F is a longitudinal cross-section of a delivery tube distal portion embodying features of the invention having a tab configured to retain and align a plug, and containing a plug configured to be retained by a tab.

A delivery tube 14 may be configured to retain and optionally to align a plug 26. For example, a delivery tube 14 may have a retaining feature 64, illustrated in FIGS. 4D, 4E and 4F as a tab, configured to engage a plug 26 and to hold it in place. The retaining feature 64 shown in FIG. 4D is a tab of metal formed by two longitudinal slots in the distal end of the wall 46 of delivery tube 14 that has been deflected inwardly to engage a plug 26 disposed within the bore 16, as shown in FIGS. 4E and 4F (the tab shown in FIG. 4F may be formed by one radial and two longitudinal slots). A retaining feature 64, such as a tab, may also help to align a plug 26 within a delivery tube 14. A plug 26 may optionally also be configured to be retained by a retaining feature 64, such as a tab, as illustrated in FIGS. 4E and 4F, although a retaining feature 64 may be effective to retain a plug 26 without any particular configuration of a plug 26. A plug 26 may also be configured to be aligned by a retaining feature 64, e.g., by having a notch, depression, ridge or other feature configured to engage a retaining feature 64.

Upon expulsion of a plug 26, as may be caused by distal movement of a plunger 28, a retaining feature 64 may become reconfigured to allow passage of a marker 24 out of an orifice 34 for delivery into a patient. For example, where the retaining feature 64 is a tab intruding into a tube bore 16, as shown in FIGS. 4D, 4E and 4F, the expulsion of a plug 26 may be effective to bend the tab outwardly so it more closely approaches tube wall 46 and does not prevent movement of a marker 24 through the bore 16 of a delivery tube 14. Alternatively, a retaining feature 64 may be unaffected by movement of a plug 26 or a marker 24. For example, a retaining feature 64 may be configured to impede movement of a plug 26 or of a marker 24, without preventing such movement, and so act to releasably retain a plug 26 effective to retain a marker 24 within a delivery tube 14 until the delivery of the marker 24 is desired.

Several examples of alternative embodiments of retaining features 64 are illustrated in FIGS. 5A through 5H, representing some, but not all, suitable types and configurations of retaining features 64 embodying features of the invention. A retaining feature 64 may be disposed at any location on, within, or through a wall 46 of delivery tube 14, although a distal portion 18 of a delivery tube 14 is preferred. A retaining feature may be continuous with an orifice 34 at the distal tip 36 of a delivery tube, or may be disposed proximally of the distal tip 36 of a delivery tube 14. A delivery tube 14 may include more than one retaining feature 64, and may include more than one shape or type of retaining feature 64.

Figure 5E:
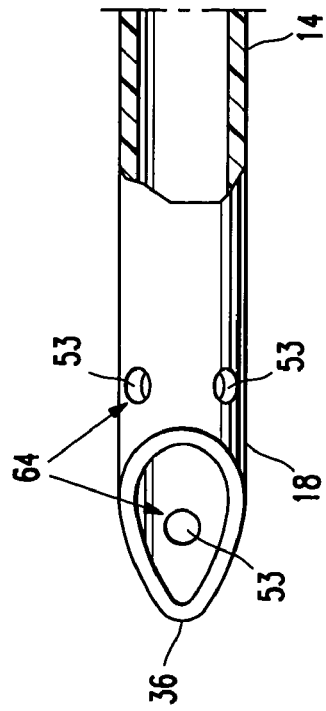
Figure 5G:
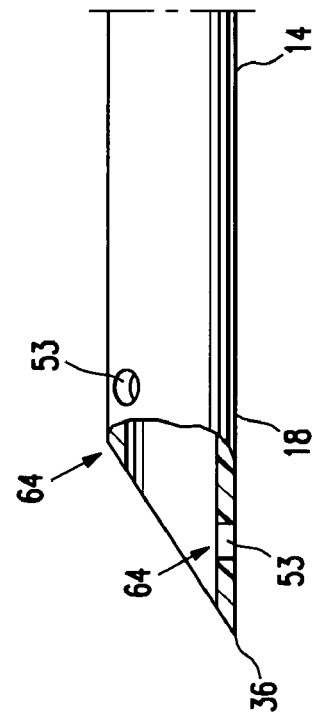
Figure 5F:
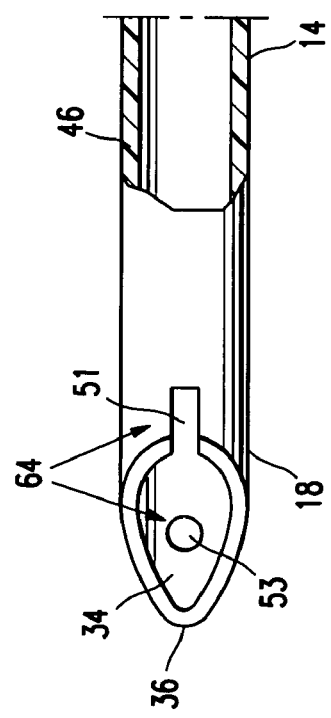
Figure 5H:
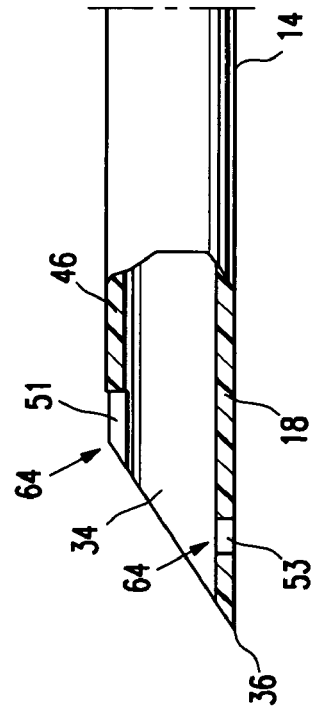

FIG. 5A is a plan view, and FIG. 5B is an elevation view, of a distal portion 18 of a delivery tube 14 of a marker delivery device 12 embodying features of the invention, with a retaining feature 64 that is a rectangular slot 51 through tube wall 46. In FIGS. 5C and 5D, a distal portion 18 of a delivery tube 14 is shown having two retaining features 64: a rectangular slot 51 and a round hole 53 through tube wall 46. The distal portion 18 of delivery tube 14 shown in FIGS. 5E and 5F has retaining features 64 that are a round hole 53 and a rectangular slot 51 connecting to orifice 34. The retaining features 64 illustrated in FIGS. 5G and 5H are all round holes 53 spaced around delivery tube 14. Retaining features 64 may also take other shapes and may be disposed in other positions on a distal portion 18. For example, a retaining feature may be an irregularly-shaped slot, combining in part a round hole and a slot with angled sides, and may connect with orifice 34 at tube distal tip 36.

A marker delivery assembly 10 embodying features of the invention may be used to deliver a marker 24 to a desired location within a patient's body. Such a desired location is typically a lesion site from which a biopsy sample has been, or is to be, taken, or a lesion has been or will be removed. Assemblies, devices, and methods embodying features of the invention find use, for example, in marking a breast biopsy site. By way of illustration, the use of assemblies, devices and methods embodying features of the invention will be discussed below in terms of breast biopsies and similar uses involving marking sites within a breast of a human female. It will be understood that the assemblies, devices and methods embodying features of the invention find use in a variety of locations and in a variety of applications, in addition to the human breast.

Figure 6:
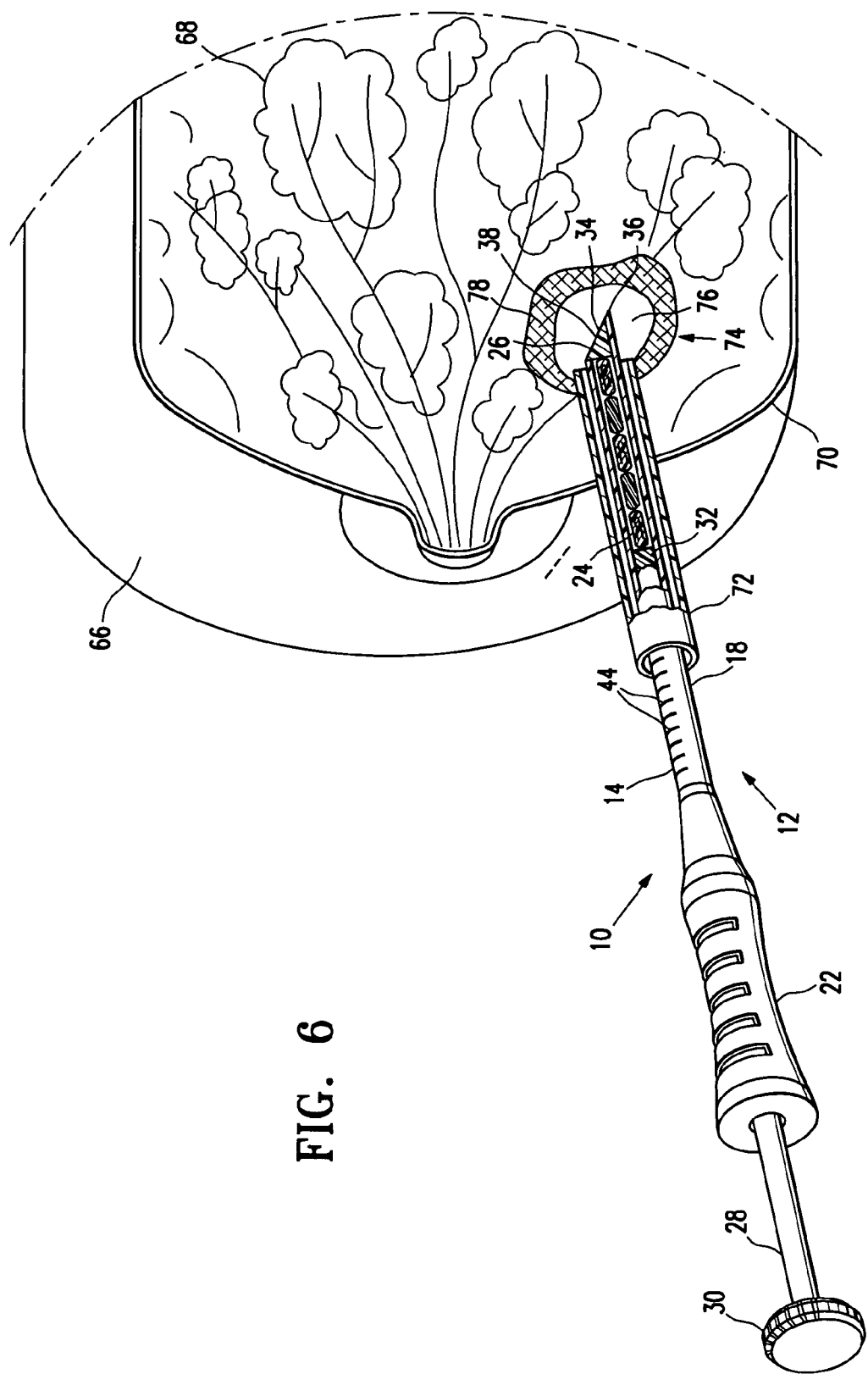
FIG. 6 is a partially cut away, perspective view of a human breast having a lesion from which a biopsy specimen has been removed, and showing a guide cannula and a marker delivery assembly embodying features of the invention inserted into the breast, the assembly having markers and a plug configured to retain the markers within a delivery tube of a delivery device.

An assembly 10 or delivery device 12 can be inserted into a breast 66 through a guide cannula 72, as illustrated in FIG. 6. Alternatively, an assembly 10 or delivery device 12 can be inserted directly into a breast 66, using a distal tip 36 that is sharp and so is configured to pierce or puncture tissue 68, with or without an initial incision through the skin 70 of a patient. In either case, markings 44 along a delivery tube 14 may be used to aid in the proper placement of the orifice 34 of a delivery tube 14, and so to aid in the proper delivery of a marker 24 to a desired location within a breast.

A plug 26 and marker 24 may be introduced into a breast 66 of a patient at a lesion site 74 adjacent or within a biopsy cavity 76, from which a biopsy sample or tissue from a lesion has been taken, as illustrated in FIG. 6. Alternatively, a plug 26 and marker 24 may be introduced into a patient's body in the absence of a biopsy cavity. This could be useful, for example, to mark a location from which to take a biopsy at a later time. A lesion site 74 may be the site of a suspected lesion, or a lesion site 74 may be the site of a known lesion. A biopsy cavity 76 may be an existing cavity, filled, if at all, with gas or fluid, or may be a virtual cavity, substantially filled with tissue that has collapsed into, or grown into, a site from which tissue has been previously removed. A biopsy cavity 76 may adjoin, or be lined with, or be at least in part surrounded by suspicious tissue 78, which may be remaining tissue of a lesion, newly grown tissue at least partially filling a biopsy cavity, tissue injured when the biopsy was taken, or other tissue.

Assemblies, devices and methods embodying features of the invention may be used to deliver a marker to a desired location within a body of a patient, by inserting a delivery device 12 into a patient having markers 24 retained within the bore 16 of the delivery tube 14 by a plug 26, and expelling a marker 24 from the orifice 34 into the desired location. A marker 24 may be expelled, for example, by depressing plunger 28 by moving plunger handle 30. Depression of plunger 28, pushing on a marker 24, is preferably effective to expel plug 26 from the orifice 34, allowing a marker 24 to exit the delivery tube 14 for delivery within a patient.

An operator may grasp a device handle 22 to guide the device 12 during insertion, and to steady the device 12 during depression of the plunger 28. Insertion of a device 12 results in the placement of at least a portion of the device 12 adjacent a desired location. The device 12, in particular the distal tip 36 and orifice 34 of the device 12, may be guided adjacent a desired location such as a lesion site, or a biopsy cavity, or other internal body site where delivery of a marker 24 is desired.

An initial scalpel incision in the skin is typically made in order to introduce a device 12 into the body tissue of a patient, although in many cases the sharp edge 34 or pointed tip 36 tip may be used to gain access to tissue beneath the skin without the use of an incision by a surgical tool. Insertion of the device 12 into a patient, e.g. into a breast 66 of a patient, may be guided by an operator with the aid of an imaging device. A delivery tube 14, and/or markings 44, as well as markers 24 and optionally plug 26, may be detectable by an imaging device, such as an ultrasound imaging device, an X-ray imaging device, a magnetic resonance imaging device, or other imaging device. Alternatively, or additionally, insertion may be visually guided, or may be guided by palpation or by other means.

As illustrated in FIG. 6, insertion of the device 12 into a patient, e.g. into a breast 66 of a patient, may be guided by a guide cannula as well. Such insertion may be performed with or without the aid of an imaging device, such as an ultrasound imaging device, an X-ray imaging device, a magnetic resonance imaging device, or other imaging device. Alternatively, or additionally, insertion may be visually guided, or may be guided by palpation or by other means.

A plug 26 may be made with any suitable material. Typically, a plug 26 is made with the same materials as a marker 24. A plug 26 may serve as a marker after its expulsion from orifice 34 and placement into a patient's body. Preferably, a plug 26 is made with a biocompatible material, and provides sufficient structural strength as to retain a marker 24 within a delivery tube 14 and, where insertion of a delivery device embodying features of the invention is performed without the aid of a guide cannula, a material used in making a plug 26 preferably has sufficient structural strength to withstand the forces encountered during insertion into tissue or through skin. Materials suitable for use in making a plug 26 embodying features of the invention include polymers, plastics, resins, waxes, glasses, ceramics, metals, metal oxides, and composites, combinations and mixtures of these materials. For example, a wax such as bone wax, or other biocompatible material is suitable for use in making a plug 26. In presently preferred embodiments, a plug 26 is made with bioresorbable polymers such as poly-lactic acid and poly-glycolic acid. A plug may be made of more than one material, as illustrated, for example, in FIG. 3D, showing a plug 26, which may be made primarily with a plastic or a polymer, and having an internal retention element 60, which may be, for example, a metal clip or spring.

A marker 24, including a plug 26 when configured to also serve as a marker 24, is preferably readily visible by ultrasonic imaging (USI), or by conventional imaging methods, such as x-ray and magnetic resonance imaging methods, or by more than one imaging technique. Suitable bio-compatible materials which may be used in a marker 24 or a plug 26 include polyethylene, polytetrafluoroethylene, PEBAX (made by Autochem Corp.), and the like.

Thus, biocompatible plugs 26 or markers 24 embodying features of the invention are preferably made using materials including a bioresorbable material. Some particularly suitable bioresorbable materials include bio-resorbable polymers including, but not limited to, polymers of lactic acid, glycolic acid, caprolactones, and other monomers; thus, for example, suitable bio-resorbable polymers may include poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), poly(urethanes), poly(ester urethanes), polysaccharides, polylactic acid, polyglycolic acid, polycaproic acid, polybutyric acid, polyvaleric acid, and copolymers, polymer alloys, polymer mixtures, and combinations thereof.

A marker 24 typically should remain in place and detectable within a patient for up to at least 2 weeks to have practical clinical value. Thus, a marker 24, including a plug 26 configured to serve as a marker, is detectable at a biopsy site within a patient for a time period of at least 2 weeks, preferably at least about 6 weeks, and may remain detectable for a time period of up to about 20 weeks, more preferably for a time period of up to about 12 weeks. In some embodiments, a marker material for use in markers 24 and plugs 26 embodying features of the invention is preferably not detectable about 6 months after placement at a biopsy site, and is more preferably not detectable with ultrasound about 12 weeks after placement at a biopsy site. Thus, a preferable in-vivo lifetime for a marker material for use in markers 24 and plugs 26 having features of the invention is between about 6 weeks and about 12 weeks.

In embodiments of the invention, a marker 24, and a plug 26 configured to serve as a marker 24 following expulsion from a delivery tube 14, may be detectable by ultrasound. Ultrasound-detectable markers 24 and plugs 26 may be formed with ultrasound detectable materials, such as stainless steel, titanium, platinum and the like, other bio-compatible metals, ceramics, metal oxides or polymers, or composites or mixtures of these materials. Typically, any material which reflects ultrasound energy may be suitable for use in an ultrasound-detectable marker. For example, materials having bubbles, internal voids, or gas-filled spaces, are detectable by ultrasound. A marker 24 or a plug 26 may be formed so as to include voids, such as cavities, to enhance their detectability by ultrasound. For example, a cavity size of between about 10 microns and about 500 microns, preferably between about 50 microns to about 200 microns, may be suitable to enhance the ultrasound-detectability of a marker 24 or plug 26.

Plugs 26 and markers 24 are configured to fit within a bore 16 of a delivery tube 14. A delivery tube 14 maybe configured to fit within a guide cannula 72, such as a guide cannula sized to accept a Mammotome®, Tru-Cut®, or SenoCor® biopsy device. Typically, a plug 26 or marker 24 will have a diameter determined by the size of a bore 16, typically between about 0.02" (0.5 mm) and about 0.5" (12 mm), preferably between about 0.04" (1 mm) and about 0.3" (8 mm). In addition, a plug 26 or marker 24 may have a length of between about 0.04" (1 mm) and about 0.8" (20 mm), preferably between about 0.1" (2.5 mm) and about 0.6" (15 mm).

A radiopaque element 40 may be made with any suitable radiopaque material, including stainless steel, platinum, gold, iridium, tantalum, tungsten, silver, rhodium, nickel, bismuth, other radiopaque metals, alloys and oxides of these metals, barium salts, iodine salts, iodinated materials, and combinations of these. Radiopaque materials and markers may be permanent, or may be temporary and not detectable after a period of time subsequent to their placement within a patient. MRI contrast agents such as gadolinium and gadolinium compounds, for example, are also suitable for use with plugs 26 and/or markers 24 embodying features of the invention. Colorants, such as dyes (e.g., methylene blue and carbon black) and pigments (e.g., barium sulfate), may also be included in markers 24 and/or plugs 26 embodying features of the invention.

Markers 24, and plugs 26 configured to serve as markers, may also include other materials besides marker materials, including anesthetic agents, hemostatic agents, pigments, dyes, materials detectable by magnetic resonance imaging (MRI), inert materials, and other compounds.

In any of the above-described embodiments of the invention, a plug 26 may include an adhesive component to aid the plug 26 to adhere to a delivery tube 14. In addition, an adhesive component may be useful to aid a marker 24 (and a plug 26 after expulsion from a delivery tube 14) to adhere to adjacent tissue within the body of a patient, such as at a biopsy site. The adhesive component may comprise a biocompatible adhesive, such as a polyurethane, polyacrylic compound, polyhydroxymethacrylate, fibrin glue (e.g., Tisseal™), collagen adhesive, or mixtures thereof.

While particular forms of the invention have been illustrated and described, it will be apparent that various modifications can be made without departing from the spirit and scope of the invention. Accordingly, it is not intended that the invention be limited to the specific embodiments illustrated. It is therefore intended that this invention be defined by the scope of the appended claims as broadly as the prior art will permit, and in view of the specification if need be. All patents and patent applications referred to above are hereby incorporated by reference in their entirety.

What is claimed is:

1. An intracorporeal marker delivery device, comprising:
a delivery tube which has a tapered, tissue penetrating distal tip with an inclined distal surface, an inclined discharge orifice in the tapered distal tip adjacent the inclined distal surface, and an inner bore that extends to the inclined discharge orifice;
a plurality of remotely detectable markers, which are formed at least in part of bioresorbable material, slidably disposed within the inner bore;
a plug having a first portion, a lip portion and an inclined exposed surface, the plug being formed at least in part of bioresorbable material, the first portion of the plug being releasably secured within the inner bore of the delivery tube distal to the plurality of remotely detectable markers disposed therein to retain the plurality of remotely detectable markers within the inner bore, wherein the plug is disposed at least in part within the inclined discharge orifice of the delivery tube, the lip portion being configured to extend radially outwardly from the first portion so as to engage the inclined distal surface of the tapered distal tip of the delivery tube; and
a plunger slidably disposed within the inner bore proximal to the plurality of remotely detectable markers.

2. The delivery device of claim 1, wherein the plug comprises a permanent marker.

3. The delivery device of claim 1, wherein the plug is detectable with ultrasound.

4. The delivery device of claim 1, wherein the plug is formed at least in part of a radiopaque material.

5. The delivery device of claim 1, wherein the plug has at least one bioactive element.

6. The delivery device of claim 5, wherein at least one bioactive element is selected from the group consisting of hemostatic materials, anesthetic materials, absorbent materials, antibiotic materials, antifungal materials, antiviral materials, chemotherapeutic materials, radioactive materials, and other pharmaceutical materials.

7. The delivery device of claim 1, wherein the inclined exposed surface of the plug is positioned to correspond to the inclined discharge orifice in the tapered distal tip of the delivery tube and the first portion of the plug has a longitudinal gap.

8. An intracorporeal marker delivery device, comprising:
a delivery tube which has a tapered, tissue penetrating distal tip, an inclined discharge orifice in the tapered distal tip and an inner bore extending to the inclined discharge orifice;
a plurality of remotely detectable markers which are formed at least in part of bioresorbable material, which are slidably disposed within the inner bore and at least one of which has a permanent radiopaque element disposed therein; and
a plug, which is formed at least in part of bioresorbable material, which is releasably secured within the inner bore of the delivery tube distal to the at least one marker disposed therein, to retain the plurality of remotely detectable markers within the inner bore, and which has an inclined exposed surface, which is configured to partially occlude the inclined discharge orifice, and which allows passage of at least one marker of the orifice when released from the inner bore, wherein at least part of the plug is configured to fit tightly within at least part of the inner bore so as to be releasably secured therein.

9. The delivery device of claim 8, wherein at least part of the plug is configured to press against at least part of the inner bore.

10. The delivery device of claim 9, wherein the plug comprises an expandable element configured to urge against the inner bore.

11. The delivery device of claim 10, wherein the expandable element is selected from the group of elements consisting of a spring, a coil, a clip, a loop, an arch, and a resilient core.

12. The delivery device of claim 11, wherein the expandable element includes a radiopaque element.

13. An intracorporeal marker delivery device for delivering a plurality of remotely detectable markers to a desired site within a patient's body from which tissue has been removed, comprising:
a delivery tube which has a tapered, tissue penetrating distal tip, an inclined discharge orifice in the tapered distal tip and an inner bore extending to the inclined discharge orifice;
a plurality of remotely detectable markers which are formed at least in part of bioresorbable material, which are slidably disposed within the inner bore;
an expandable plug, which is formed at least in part of bioresorbable material, which is releasably secured within the inner bore of the delivery tube distal to the plurality of remotely detectable markers disposed therein, to retain the plurality of remotely detectable markers within the inner bore, and which has an inclined exposed surface, which is configured to partially occlude the inclined discharge orifice, and which allows passage of at least one marker of the orifice when released from the inner bore; and
a plunger slidably disposed within the inner bore proximal to the remotely detectable markers, wherein the delivery tube has a tube wall which has at least one retaining feature configured to releasably retain the expandable plug.

14. The delivery device of claim 13, wherein a delivery tube wall retaining feature includes a protuberance.

15. The delivery device of claim 13, wherein a delivery tube wall retaining feature includes a recess.

16. The delivery device of claim 13, wherein a delivery tube wall retaining feature is selected from the group consisting of notches, holes, slots, tabs, and ridges.

* * * * *